(12) United States Patent
Boppana et al.

(10) Patent No.: US 9,822,053 B2
(45) Date of Patent: Nov. 21, 2017

(54) SINGLE STEP CONVERSION OF N-BUTYRALDEHYDE TO 2-ETHYLHEXANAL

(71) Applicant: EASTMAN CHEMICAL COMPANY, Kingsport, TN (US)

(72) Inventors: Venkata Bharat Boppana, Johnson City, TN (US); Kenneth Wayne Hampton, Jr., Gilmer, TX (US); Zhufang Liu, Kingsport, TN (US); Charles Edwan Sumner, Jr., Kingsport, TN (US); Gerald C. Tustin, Kingsport, TN (US); Guy Ralph Steinmetz, Kingsport, TN (US); Melissa Page Steffey, Nickelsville, VA (US)

(73) Assignee: Eastman Chemical Company, Kingsport, TN (US)

( * ) Notice: Subject to any disclaimer, the term of this patent is extended or adjusted under 35 U.S.C. 154(b) by 136 days.

(21) Appl. No.: 15/009,098

(22) Filed: Jan. 28, 2016

(65) Prior Publication Data

US 2017/0217866 A1 Aug. 3, 2017

(51) Int. Cl.
*B01J 23/42* (2006.01)
*B01J 23/44* (2006.01)
(Continued)

(52) U.S. Cl.
CPC .............. *C07C 45/72* (2013.01); *B01J 21/063* (2013.01); *B01J 23/44* (2013.01); *B01J 35/0013* (2013.01);
(Continued)

(58) Field of Classification Search
CPC ....... C07C 45/72; B01J 35/0013; B01J 37/18; B01J 37/16; B01J 37/0221; B01J 21/063; B01J 23/44; B01J 37/0236
(Continued)

(56) References Cited

U.S. PATENT DOCUMENTS

| 3,271,327 A | 9/1966 | McEvoy et al. |
| 4,316,990 A | 2/1982 | Morris |

(Continued)

FOREIGN PATENT DOCUMENTS

| EP | 1 133 463 B1 | 12/2004 |
| WO | WO 98/18553 A1 | 5/1998 |
| WO | WO 2014/176552 A2 | 10/2014 |

OTHER PUBLICATIONS

Notification of Transmittal of the International Search Report and the Written Opinion of the International Searching Authority dated Apr. 18, 2017 for International Application No. PCT/US2017/014822.

(Continued)

*Primary Examiner* — Haytham Soliman
(74) *Attorney, Agent, or Firm* — Dennis V. Carmen; Steven A. Owen

(57) ABSTRACT

Disclosed is a method of making and using a titania supported palladium catalyst for the single step synthesis of 2-ethylhexanal from a feed of n-butyraldehyde. This titania supported palladium catalyst demonstrates high n-butyraldehyde conversion but also produces 2-ethylhexanal in an appreciable yield with maintained activity between runs. This method provides a single step synthesis of 2-ethylhexanal from n-butyraldehyde with a catalyst that can be regenerated that provides cleaner downstream separations relative to the traditional caustic route.

13 Claims, 1 Drawing Sheet

Eggshell Distribution       Egg Yolk Distribution       Uniform Distribution

*Various distributions of active catalytic sites on a particle support*

(51) Int. Cl.
| | |
|---|---|
| C07C 45/00 | (2006.01) |
| C07C 45/72 | (2006.01) |
| B01J 21/06 | (2006.01) |
| B01J 37/02 | (2006.01) |
| B01J 37/16 | (2006.01) |
| B01J 37/18 | (2006.01) |
| B01J 35/00 | (2006.01) |

(52) U.S. Cl.
CPC ....... B01J 37/0221 (2013.01); B01J 37/0236 (2013.01); B01J 37/16 (2013.01); B01J 37/18 (2013.01)

(58) Field of Classification Search
USPC .......................................................... 502/339
See application file for complete search history.

(56) References Cited

U.S. PATENT DOCUMENTS

| | | | |
|---|---|---|---|
| 4,404,124 | A | 9/1983 | Johnson et al. |
| 5,144,089 | A | 9/1992 | Arena et al. |
| 5,254,743 | A | 10/1993 | Holmgren et al. |
| 5,258,558 | A | 11/1993 | Arena et al. |
| 2011/0151354 | A1 | 6/2011 | Jin et al. |
| 2012/0149955 | A1 | 6/2012 | Fecant |
| 2014/0088326 | A1 | 3/2014 | Norman et al. |

OTHER PUBLICATIONS

Ko et al.; "Efficient direct synthesis of 2-tehylhexanal from n-butyraldehyde and hydrogen using palladium modified base catalysts"; Applied Catalysis A: General; 184; 1999; pp. 211-217.
Ko et al.; "Highly selective Pd/KX catalysts for low-pressure one-step synthesis of 2-ethylhexanal from n-butyraldehyde and hydrogen"; Catalysis Letters; 54; 1998; pp. 207-210.
Co-pending U.S. Appl. No. 15/008,516, filed Jan. 28, 2016; Boppana et al.
Iglesia et al.; "Synthesis and Catalytic Properties of Eggshell Cobalt Catalysts for the Fischer-Tropsch Synthesis"; Journal of Catalysis; 153; 1995; pp. 108-122.
Toebes et al.; "Synthesis of supported palladium catalysts"; Journal of Molecular Catalysis A: Chemical; 173; 2001; pp. 75-98.
Teranishi et al.; "Size Control of Palladium Nanoparticles and Their Crystal Structures"; Chem. Mater.; 1998; vol. 10; No. 2; pp. 594-600.
Toshima et al.; "Structural Analysis of Polymer-Protected Pd/Pt Bimetallic Clusters and Dispersed Catalysts by Using Extended X-ray Absorption Fine Structure Spectroscopy"; J. Phys. Chem.; 1991; 95; pp. 7448-7453.
Yonezawa et al.; "Novel Characterization of the Structure of Surfactants on Nanoscopic Metal Clusters by a Physicochemical Method"; Langmuir; vol. 11; No. 12; 1995; pp. 4601-4604.
Schmid et al; "$Pt_{309}Phen^*_{36}O_{30\pm10}$, a Four-Shell Platinum Cluster**"; Angew. Chem. Int. Ed. Engl.; 28; 1989; No. 6; pp. 778-780.
Schmid, Günter; "Large Clusters and Colloids. Metals in the Embryonic State"; Chem. Rev.; 1992; 92; pp. 1709-1727.
Burton, Patrick David; "Novel routes for synthesis of Pd nanoparticles and faceted ZnO supports for heterogeneous catalysts"; Dissertation; The University of New Mexico; May 2011; pp. 22-23.
Wang et al.; "Shape-dependent catalytic activity of palladium nanocrystals for the oxidation of carbon monoxide"; Catalysis Science & Technology; 2011; DOI: 10,1039/c2cy00417h.
Liang et al.; "The two-step chemical vapor deposition of Pd(allyl)Cp as an atom-efficient route to synthesize highly dispersed palladium nanoparticles on carbon nanofibers"; Chemical Communications; 2005; pp. 282-284.
Shao et al.; "A Facile and Controlled Route to Prepare an Eggshell Pd Catalyst for Selective Hydrogenation of Phenylacetylene"; ChemCatChem; 2010; 2; pp. 1555-1558.
Qiu et al.; "A Simple Preparation Method of Eggshell Ni/MgO—$Al_2O_3$ Catalyst for Partial Oxidation of Methane"; React. Kinet. Catal. Lett.; vol. 94; No. 1; 2008; pp. 149-155.
Gulková et al.; "Preparation of $M_0O_3$/MgO catalysts with eggshell and uniform Mo distribution by methanol assisted spreading: Effect of $M_0O_3$ dispersion on rate of spreading".
Wang et al.; "Development of a simple method for the preparation of novel egg-shell type Pt catalysts using hollow silica nanostructures as supporting precursors"; Materials Research Bulletin; 43; 2008; pp. 889-896.
Pérez et al.; "Shape-dependent catalytic activity of palladium nanoparticles embedded in $SiO_2$ and $TiO_2$"; Catalysis Today; 2011; pp. 1-9.
Brunauer et al.; "Adsorption of Gases in Multimolecular Layers"; J. Am. Chem. Soc.; 60; 1938; pp. 309-316.
Kelly et al; "Waste elimination in condensation reactions of industrial importance"; Green Chemistry; 2002; 4; pp. 392-399.
Hamilton et al.; "Solid base catalysts and combined solid base hydrogenation catalysts for the aldol condensation of branched and liear aldehydes"; Applied Catalysis A: General; 263; 2004; pp. 63-70.
Winter et al.; "Single-stage liquid-phase synthesis of methyl isobutyl ketone under mild conditions"; Journal of Molecular Catalysis A: Chemical; 219; 2004; pp. 273-281.
Winter et al.; "A hydrotalcite-based catalyst system for the single-stage liquid-phase synthesis of MIBK"; Applied Catalysis A: General; 307; 2006; pp. 231-238.
Zhang et al.; "Preparation and Characterization of Nanosized $TiO_2$ Powders from Aqueous $TiCl_4$ Solution"; NanoStructured Materials; vol. 11; No. 8; 1999; pp. 1293-1300.
Zhang et al.; "Preparing Single-Phase Nanocrystalline Anatase from Amorphous Titania with Particle Sizes Tailored by Temperature"; Nano Letters; 2001; vol. 1; No. 2; pp. 81-85.
Yanagisawa et al.; "Crystallization of Anatase from Amorphous Titania Using the Hydrothermal Technique: Effects of Starting Material and Tempeature"; J. Phys. Chem. B; 1999; 103; pp. 7781-7787.
Garcia et al.; "Deep oxidation of light alkanes over titania-supported palladium/vanadium catalysts"; Journal of Catalysis; 229; 2005; pp. 1-11.
Li et al.; "A titania-supported highly dispersed palladium nano-catalyst generated via in situ reduction for efficient Heck coupling reaction"; Journal of Molecular Catalysis A: Chemical; 328; 2010; pp. 93-98.
Mahata et al.; "Vapour phase hydrogenation of phenol to cyclohexanone over titania supported palladium system: A kinetic study"; Indian Journal of Chemistry; vol. 39A; Aug. 2000; pp. 856-858.

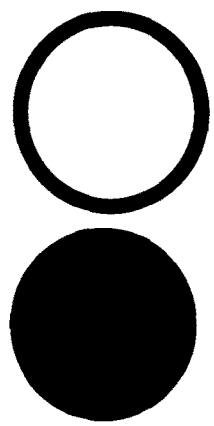 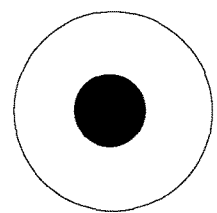
Eggshell Distribution     Egg Yolk Distribution     Uniform Distribution
*Various distributions of active catalytic sites on a particle support*

SINGLE STEP CONVERSION OF N-BUTYRALDEHYDE TO 2-ETHYLHEXANAL

FIELD OF THE INVENTION

This invention generally relates to a method for the preparation and use of an eggshell catalyst having palladium nanoparticles deposited on a titania solid support. Particularly, this invention seeks to optimize the single step conversion of n-butyraldehyde to 2-ethylhexanal through the synthesis and use of palladium nanoparticles on a titania support forming an eggshell catalyst.

BACKGROUND OF THE INVENTION

The custom design of a metal-supported catalyst is often determinative of process activity and selectivity in a reaction—crucial in almost every industrial process. Even minor adjustments to a catalyst or to catalyst synthesis conditions can drastically alter the catalytic properties, significantly impacting process activity and selectivity in a reaction.

In many reactions, metal-supported catalysts need to have the highest possible catalytically active metal surface area, or dispersion of the metal. This can be accomplished by depositing metal nano-sized particles on an inert support, which may be distributed in various configurations. Three main configurations include eggshell, egg yolk, and uniform distributions as shown in FIG. 1.

In catalysts with an eggshell distribution, the metal nanoparticles are concentrated at the exterior edge of the support. These eggshell catalysts are particularly desirable for reactions that are heat or mass transfer limited. An eggshell catalyst allows for a reaction to occur quickly on the surface of the catalyst without the pores of the catalyst becoming blocked. With an eggshell catalyst, the diffusion path length necessary for the reactants and products to travel is minimized, making this configuration best for fast reactions with strong diffusional restrictions, producing higher selectivity in reactions where diffusion is the limiting step. However, there has been limited research done in the field of eggshell catalysts due to their complexity and difficult synthetic approaches.

While the use of small metallic particles is very desirable in a catalyst, the particles have a tendency towards agglomeration. Agglomeration occurs when nanoparticles clump together, bonding with other metallic nanoparticles to form large clusters, typically around 20 to 100 nm. Due to the high expense of most metals as well as dispersion and surface area considerations as mentioned above, agglomeration typically renders synthesis of 2 nm particles on a catalyst support a very difficult process.

Currently in the art, various methods have been employed to synthesize a metal nanoparticle catalyst. One such method consists of using capping agents to prevent the metallic nanoparticles from bonding with one another. Capping agents bind with the catalyst to control the structural characteristics and prevent agglomeration of the particles. Capping agents however, act as a physical barrier to the reactants, restricting access to the catalyst and therefore must be removed before the actual reaction can begin. This creates a very short window of opportunity in which the reaction must take place, while the catalyst is active but before the particles agglomerate.

Other methods used to synthesize metallic nanoparticle catalysts are surfactants, calcination, chemical vapor techniques, carbon monoxide, custom supports, manipulation of pH levels, manipulation of pressure conditions, and long preparation times. Many of these reactions can require difficult techniques and can be very costly, particularly on a large scale. In addition, most of these metallic nanoparticle catalysts are not synthesized in an eggshell formation, as there has been little research done in this field to-date and the current synthesis is quite difficult. Most catalysts are produced with a uniform configuration, with a few in egg yolk configurations, and fewer still in the desirable eggshell configuration.

Catalysts are often used in hydrogenation reactions. There has been a long-felt but unsolved need in the chemical industry for an easier, quicker, and more affordable alternative to produce desirable catalyst compositions without the requisite laborious synthesis to be used in selective hydrogenation reactions. Even small improvements in reducing production costs can generate substantial savings. By cutting out wasteful steps and extra reaction requirements, the savings of time and money could be exponential.

The synthesis of 2-ethylhexanal via an aldol condensation reaction exemplifies a compound that is selectively hydrogenated without removing the aldehyde functionality. 2-Ethylhexanal is an important industrial chemical finding uses in a variety of applications such as perfumes, synthetic precursors for plasticizers, and 2-ethylhexanoic acid. The synthesis of 2-ethylhexanal disclosed in the art typically requires several synthetic steps, high pressures, multiple catalysts, and/or complex catalysts.

Using a palladium on titania eggshell type catalyst eliminates the need for a homogeneous catalyst to promote the aldol reaction to make 2-ethylhexenal. Typically, the aldol reaction is base catalyzed, using a caustic reagent such as sodium hydroxide. Although effective, this type of base catalysis can be problematic as it requires special handling of the base, downstream separation of the homogeneous base, and higher capital costs. Typically in these applications, the caustic catalyst is not separated but requires additional treatments of the waste stream to meet regulatory requirements. Furthermore, this synthetic approach increases costs as the catalyst is not recovered but wasted downstream.

The present invention would allow for a facile synthesis of a palladium eggshell catalyst using easily-controllable, various sized nanoparticles in a desirable eggshell formation. This catalyst synthetic scheme allows for a one-step reaction, occurring at atmospheric pressure, without the manipulation of reaction pH, the use of surfactants, capping agents, carbon monoxide, or chemical vapor deposition. The preparation time is relatively short and a custom support is not required. By varying only the reducing agent used in the reaction, eggshell distributed metal catalysts can be synthesized with varying nanoparticle sizes.

This inventive palladium on titania eggshell catalyst is able to use n-butyraldehyde as a feed towards the single-step synthesis of 2-ethylhexanal. Using this palladium on titania eggshell catalyst to convert n-butyraldehyde to 2-ethylhexanal provides several benefits not disclosed together in the art such as: 1) a single-step synthetic scheme; 2) the use of a single regenerable heterogeneous palladium on titania eggshell catalyst; 3) a synthesis performed at atmospheric pressure; and 4) a reaction providing a cleaner product separation downstream due to the lack of catalyst separation or disposal.

SUMMARY OF THE INVENTION

The present invention provides in a first embodiment a method for preparing a palladium eggshell type catalyst comprising: dissolving a palladium salt in a solvent to produce a palladium salt-containing solution; mixing the palladium salt-containing solution with a titania support under atmospheric pressure; removing said solvent to produce a palladium salt-deposited support; and reducing said palladium salt-deposited support to form a palladium eggshell type catalyst using a reducing agent selected from the group consisting of: hydrogen gas, hydrogen gas mixtures, alcohol solutions, alcohol/water solutions, hydrazine solutions, and hydrazine/solvent solutions; wherein the palladium shell deposited on the titania support comprises nano-sized particles of palladium having a diameter less than about 10 nanometers; and wherein the palladium shell deposited on the titania support is concentrated within about 300 micrometers of the eggshell type catalyst's exterior surface.

The present invention provides in a second embodiment a method for the single step synthesis of 2-ethylhexanal comprising: contacting n-butyraldehyde and a hydrogen gas with a palladium on titania eggshell type catalyst under vapor-phase condensation conditions to obtain a reaction product comprising 2-ethylhexanal; wherein the palladium eggshell catalyst comprises a palladium shell deposited on a titania support comprising nano-sized particles of palladium having a diameter less than about 10 nanometers; and wherein the palladium shell deposited on the titania support is concentrated within about 300 micrometers of the palladium eggshell type catalyst's exterior surface.

The present invention provides in a third embodiment a method for the single step synthesis of 2-ethylhexanal comprising: contacting n-butyraldehyde and a hydrogen gas with a palladium on titania eggshell type catalyst under vapor-phase condensation conditions at about atmospheric pressure to obtain a reaction product comprising 2-ethylhexanal; wherein the palladium eggshell catalyst comprises about 0.1 weight % of a palladium metal shell deposited on a titania support comprising nano-sized particles of palladium having a diameter less than about 2 nanometers; and wherein the palladium shell deposited on the titania support is concentrated within about 300 micrometers of the palladium eggshell type catalyst's exterior surface.

BRIEF DESCRIPTION OF THE DRAWINGS

FIG. 1 is a picture showing various distributions of active catalytic sites on a particle support.

DEFINITIONS

The phrases "eggshell configuration" or "eggshell distribution", as used herein, are defined as a distribution of particles in which at least about 90% of the particles are located within about 300 micrometers of an exterior surface.

The phrases "egg yolk configuration" or "egg yolk distribution", as used herein, are defined as a distribution of particles in which a majority of particles are located in the center of the particulate support.

The terms "uniform configuration" or "uniform distribution" are defined as a distribution of particles in which a majority of particles are homogenously located throughout the particulate support.

The phrase "heat transfer limited reaction", as used herein, is defined as a reaction limited by the transfer of heat in which the reaction rate is less than maximum due to the heat transfer process being slower than the intrinsic reaction rate.

The phrase "heterogeneous supported catalyst", as used herein, is defined as a catalyst where the phase of the catalyst is different from the phase of the reactants or products.

The phrase "homogenous catalyst", as used herein, is defined as a catalyst where the phase of the catalyst is the same as the phase of the reactants or products.

The phrases "less than 2 nm", "less than 5 nm", "less than 7 nm", as used herein, refer to a size between 0 and about 2.0 nm, between 0 and about 5.0 nm, between 0 and about 7.0 nm, respectively, including all values in between, including whole numbers such as 0, 1, 2, fractional numbers, such as 0.5, 1.6, 1.87, 1.4445, and the endpoints such as 0 and 2.0.

The phrase "mass transfer limited reaction", as used herein, is defined as a reaction limited by the transfer or mass in which the reaction rate is less than maximum due to the transfer of mass process being slower than the intrinsic reaction rate.

The phrases "nano-sized particle" or "nanoparticle", as used herein, are defined as a particle of any shape with dimensions of about less than 100 nanometers (nm).

The phrase "noble metal", as used herein, is defined as a metal that is resistant to corrosion and oxidation in moist air. Noble metals include but are not limited to ruthenium (Ru), rhodium (Rh), palladium (Pd), silver (Ag), osmium (Os), iridium (Ir), platinum (Pt) and gold (Au).

The phrases "selective hydrogenation" or "selective hydrogenation reaction", as used herein, are defined as chemically treating a compound with hydrogen to reduce or saturate a particular element of the compound without altering another desired element of the compound.

DETAILED DESCRIPTION

It has been surprisingly discovered that an eggshell catalyst prepared from casting a palladium salt on a titania support and selectively reducing the salt to zero-valent palladium forms a shell of palladium nanoparticles on the titania support with the size of the nanoparticles depending on the method of reduction. The palladium eggshell catalyst made from this method offers a variety of catalysts having active shells comprising palladium nanoparticles of varying sizes that exhibit different capabilities of converting n-butyraldehyde to 2-ethylhexanal in a single reaction step.

2-Ethylhexanal derivatives are important industrial chemicals. A typical reaction scheme for the synthesis of these derivatives is presented below. The propylene oxo reaction yields n-butyraldehyde which can then react with itself via an Aldol Reaction to form 2-ethyl-3-hydroxyhexanal which can then eliminate water to form 2-ethylhexenal to complete the Aldol Condensation. This 2-ethylhexenal can then be selectively hydrogenated over a Pd catalyst to yield 2-ethylhexanal or over a Cu or Ni catalyst to produce 2-ethylhexanol. The phrase "2-ethylhexanal derivatives", as used herein, is defined as the 2-ethyl-3-hydroxyhexanal, 2-ethylhexenal, 2-ethylhexanal, and 2-ethylhexanol compounds. Depending on the 2-ethylhexanal derivative desired, a catalyst that could preferentially produce a desired derivative could significantly reduce process costs and increase profitability for these applications.

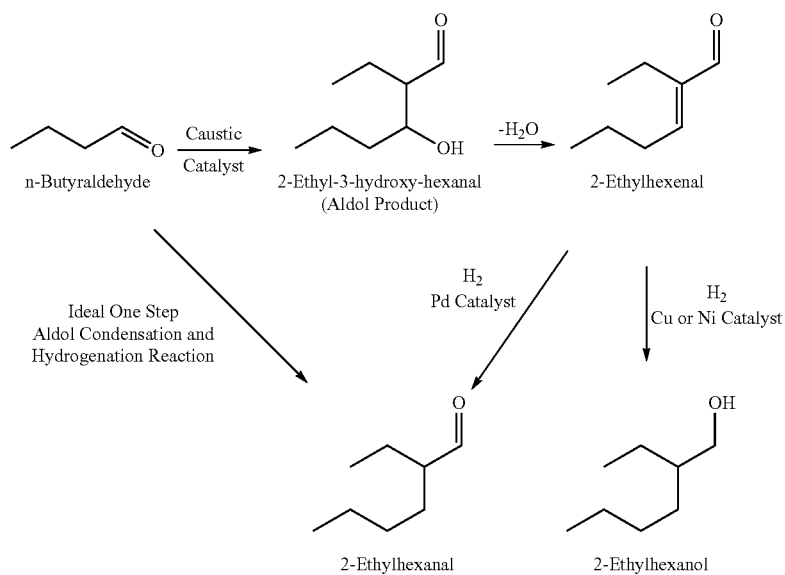

In this inventive 2-ethylhexanal synthetic process, a reactant stream of n-butyraldehyde is condensed with itself over a simple regenerable heterogeneous catalyst. This process aides in downstream separations since the catalyst would not be a part of the reactor effluent. This is unlike many current caustic processes used in the art where the caustic catalyst needs to be efficiently separated and recycled or treated before disposal.

The present invention provides in a first embodiment a method for preparing a palladium eggshell type catalyst comprising: dissolving a palladium salt in a solvent to produce a palladium salt-containing solution; mixing the palladium salt-containing solution with a titania support under atmospheric pressure; removing said solvent to produce a palladium salt-deposited support; and reducing said palladium salt-deposited support to form a palladium eggshell type catalyst using a reducing agent selected from the group consisting of: hydrogen gas, hydrogen gas mixtures, alcohol solutions, alcohol/water solutions, hydrazine solutions, and hydrazine/solvent solutions; wherein the palladium shell deposited on the titania support comprises nano-sized particles of palladium having a diameter less than about 10 nanometers; and wherein the palladium shell deposited on the titania support is concentrated within about 300 micrometers of the eggshell type catalyst's exterior surface.

The term "eggshell catalyst", as used herein, is a heterogeneous supported catalyst with homogeneously dispersed zero-valent palladium nanoparticles precisely dispersed at the outer region of the catalyst that can be used to increase both the activity and selectivity of a reaction. In some embodiments, the eggshell catalyst can have the zero-valent palladium with other noble metals to make up the nanoparticles dispersed on the solid support. Such eggshell catalysts are beneficial since they may be recycled in a one-step process or reused as a solid support unlike homogeneous catalysts. Ideally, the eggshell catalyst is tuned to have the highest catalytically active palladium surface area (i.e. dispersion of metal) for a given type of reaction. As opposed to a uniform or egg yolk distribution of the palladium (FIG. 1), an eggshell catalyst is preferred because the active palladium is concentrated at the exterior of the support. This type of catalyst could exhibit high turnovers while also being suitable for reactions that are heat and mass transfer limited. Depending on the type of reducing agent used, the inventive eggshell catalyst herein can have tailored palladium nanoparticles with customized metal surface areas along the solid oxide support.

Examples of noble metal salts include, but are not limited to, palladium salts, ruthenium salts, rhodium salts, silver salts, osmium salts, iridium salts, platinum salts, gold salts, and combinations thereof. Examples of palladium salts include, but are not limited to, palladium acetate, palladium bromide, palladium chloride, palladium cyanide, palladium iodide, palladium nitrate, palladium sulfate, tetraaminepalladium bromine, tetraaminepalladium chloride, (ethylenediamine)palladium(II) chloride. Examples of ruthenium salts include, but are not limited to, ruthenium acetate, ruthenium chloride, ruthenium iodide, ruthenium nitrosyl chloride, ruthenium nitrosyl nitrate, chloropentaamineruthemium chloride, hexaamineruthenium chloride, pentaammineruthernium chloride. Examples of rhodium salts include, but are not limited to, rhodium acetate, rhodium chloride, rhodium nitrate, rhodium sulfate, rhodium heptafluorobutyrate, diammonium sodium hexanitrorhodate. Examples of silver salts include, but are not limited to, silver acetate, silver bromate, silver carbonate, silver chlorate, silver chloride, silver chromate, silver citrate, silver cyanate, silver cyanide, silver cyclohexanebutyrate, silver fluoride, silver heptafluorobutyrate, silver hexafluoroantimonate, silver hexafluoroarsenate, silver hexafluorophosphate, silver iodide, silver lactate, silver metavandate, silver molydbate, silver nitrate, silver nitrite, silver pentafluoropropionate, silver perchlorate, silver perrhenate, silver phosphate, silver sulfadizine, silver sulfate, silver tetrafluoroborate, silver thiocyanate, silver p-toluene sulfonate Examples of osmium salts include, but are not limited to, osmium acetate, osmium chloride, pentammine(trifluoromethanesulfonato)osmium (III) triflate. Examples of iridium salts include, but are not limited to, iridium acetate, iridium bromide, iridium chloride, pentaamminechloroiridium chloride, tetrairidium dodecacarboynl, hydrogen hexachloroirididate. Examples of platinum salts include, but are not limited to, platinum acetate, platinum bromide, platinum chloride, platinum cyanide, platinum iodide, trans-platinum(II)diammine dichloride, tetraammineplatinum hydrogent carbonate, cis-diamminetetrachloroplatinum, trans-diamminetetrachloroplatinum, hydrogen hexabromoplatinate, hydrogen hexahydroxyplatinate. Examples of gold salts include, but are not limited to, gold acetate, gold bromide, gold chloride, gold hydroxide, gold iodide, hydrogen tetrabromoaurate and potassium gold chloride.

In some examples, the palladium salt comprises palladium acetate, palladium bromide, palladium chloride, palladium cyanide, palladium iodide, palladium nitrate, palladium sulfate, tetraaminepalladium bromine, tetraaminepalladium chloride, (ethylenediamine)palladium (II) chloride, or combinations thereof. In some examples, the ruthenium salt comprises ruthenium salts such as ruthenium chloride, ruthenium iodide, ruthenium nitrosyl chloride, ruthenium nitrosyl nitrate, chloropentaamineruthemium chloride, hexaamineruthenium chloride, pentaammineruthernium chloride, or combinations thereof. In some examples, the platinum salt comprises platinum acetate, platinum bromide, platinum chloride, platinum cyanide, platinum iodide, trans-platinum(II)diammine dichloride, tetraammineplatinum hydrogent carbonate, cis-diamminetetrachloroplatinum, trans-diamminetetrachloroplatinum, hydrogen hexabromoplatinate and hydrogen hexahydroxyplatinate, or combinations thereof.

In other examples, the palladium salt comprises palladium acetate, palladium bromide, palladium chloride, palladium cyanide, palladium iodide, palladium nitrate and palladium sulfate, or combinations thereof. In yet other examples, the noble metal salt or palladium salt is palladium acetate.

Dissolving a noble metal salt in a solvent to produce a noble metal-salt-containing solution can be performed at a variety of concentrations and conditions. For example, the palladium salt can be dissolved in the solvent to form an about 0.1% to about 20% by weight, an about 0.1% to about 10% by weight, or an about 0.2% to about 5% by weight of said noble metal salt in a solvent to produce a palladium salt-containing solution. The salt-containing solution can be made at atmospheric pressure and at any temperature from 0° C. up to the boiling point of the solvent used. The phrase "dissolving", as used herein, means for the solid palladium salt to pass into solution and become part of the liquid phase; the palladium salt may completely dissolve or only partially dissolve into the solvent. In some embodiments, the palladium salt is completely dissolved into a solvent to produce a palladium salt-containing solution.

Examples of solvents include, but are not limited to, water and/or one or more organic solvents such as acetone, methyl acetate, ethyl acetate, methyl ethyl ketone, methyl isobutyl ketone, methyl n-butyl ketone, benzene, toluene, xylenes, napthalenes, n-hexane, n-heptane, pentane, cyclohexene, cyclohexane, petroleum ether, formaldehyde, glutaraldehyde, carbon disulphide, pyridine, amides, amines, trichloroethane, trichloroethylene, methylene chloride, chloroform, carbon tetrachloride, tetrachloroethylene, and mixtures thereof. In some embodiments, the solvent is acetone.

The wetness impregnation method comprises mixing the palladium salt-containing solution with a solid oxide support under atmospheric pressure for a limited amount of time at a given temperature. To effectively impregnate the solid oxide support, the palladium salt-containing solution and solid oxide support should be shaken or mixed together for about 5 seconds to about 30 minutes, about 5 seconds to about 15 minutes, about 5 seconds to about 10 minutes, about 5 seconds to about 5 minutes, about 5 seconds to about 1 minute, or for about 30 minutes, about 25 minutes, about 20 minutes, about 15 minutes, about 10 minutes, about 5 minutes, about 1 minute, about 45 seconds, about 30 seconds, or about 15 seconds. The temperature for the wetness impregnation method can be any temperature from about 0° C. up to the boiling point of the solvent used. In some embodiments, it can be useful to incorporate the palladium salt-containing solution with a solid oxide support that has a complimentary pore volume to produce a palladium-salt-deposited support with varying thicknesses of the noble metal salt.

The solid oxide support comprises aluminum oxide, $\Theta$-$Al_2O_3$, titanium oxide, $TiO_2$, titania, zirconium oxide, titanium (IV) oxide, manganese oxide, copper oxide, iron oxide, scandium oxide, yttrium oxide, hafnium oxide, vanadium pentoxide, tantalum pentoxide, niobium pentoxide, tin oxide, zinc oxide, alumina zirconia, ceria zirconia, zirconia, zirconium silicate, zeolites, clay, or mixtures thereof. In some embodiments, the solid oxide support comprises titanium dioxide, titanium (IV) oxide, titania, or $TiO_2$. Each of these titanium dioxide, titanium (IV) oxide, titania, and $TiO_2$ materials exist and can be used in the anatase, rutile, and brookite mineral forms. In some embodiments, the titanium dioxide, titanium (IV) oxide, titania, and $TiO_2$ materials are used in the anatase form. In other embodiments, the titanium dioxide, titanium (IV) oxide, titania, and $TiO_2$ materials are used as a mixture of the anatase and rutile forms. In some embodiments, the solid oxide support is titania in the anatase mineral form. The supports should be physically robust and pre-shaped. The term "pre-shaped" is used in this context to mean that the shape of the final catalyst is essentially the same as the starting support. The pre-shaped oxides typically can have average particle diameter sizes ranging from about 0.1 millimeter (mm) to about 20 mm. They can be in any common form such as extrudates, compressed pellets, or bulk solid that has been pulverized to the desired mesh size. They may also be in a variety of shapes such as rods, stars, cylinders, spheres, or broken chunks. Many of these oxide supports are available commercially, and their use simplifies the preparation of the catalyst composition of the invention, although this is not a requirement of the invention.

Removing the solvent from the palladium salt-containing solution and solid oxide support to produce a palladium-salt-deposited oxide support may be performed by using any known evaporation techniques. Evaporation includes but is not limited to spontaneous evaporation in open air, evaporation through the application of heat directly from a heating source to the vessel containing the liquid, evaporation through the direct or indirect application of heat, as by means of steam, with or without pressure, or evaporation under reduced pressure, or similar techniques known in the art. In some embodiments, removing the acetone solvent from the palladium salt-containing solution and titania support to produce a palladium-salt-deposited support may be performed using any known evaporation techniques.

After the removal of the solvent from the palladium salt-containing solution and solid oxide support, a palladium-salt-deposited oxide support remains. This palladium-salt-deposited oxide support may comprise any combination of noble metal salts listed herein coated on the surface of any of the solid oxide supports listed herein. In some embodiments, the palladium-salt-deposited oxide support comprises palladium acetate on a titania oxide support.

The method of reducing the palladium-salt-deposited oxide support to form an eggshell type catalyst is important in determining the size of the zero-valent nano-sized particles of the palladium making up the shell of the catalyst.

For example, reducing the palladium-salt-deposited oxide support with a hydrogen gas in helium gas mixture produces nano-sized particles of the zero-valent palladium having a particle size of less than about 2 nm. Reducing the palladium-salt-deposited oxide support with a methanol and water mixture produces nano-sized particles of the zero-valent palladium having a particle size of less than about 5 nm. Reducing the palladium-salt-deposited oxide support with a hydrazine and acetone mixture produces nano-sized particles of the zero-valent palladium having a particle size of less than about 7 nm. Depending on the method of reduction for the palladium-salt-deposited oxide support made from using the wetness impregnation method, a shell of nanoparticles can be made with controlled sizes to offer varying surface areas for the eggshell catalyst.

The palladium shell or noble metal shell comprises nano-sized particles of palladium or a mixture of palladium with additional catalytic noble metals, such as platinum, rhodium, ruthenium, silver, iridium, osmium, and gold. In some embodiments, the palladium shell is entirely palladium. In other embodiments, palladium and platinum are the noble metals used in the shell. The palladium or noble metal shells can be made as disclosed above using any of the known salts of these palladium, platinum, rhodium, ruthenium, silver, iridium, osmium, or gold noble metals.

A majority of the palladium nanoparticles making up the noble metal shells of these eggshell catalysts are located within about 300 micrometers ("microns") from the exterior surface of the catalyst composition to form an eggshell distribution. A "majority", as used herein, means that more particles are located within a given range than the amount of particles located outside of the range. For example, 50.01% or more of the noble metal nanoparticles of the noble metal shell may be located or concentrated within 0-300 microns, 0-275 microns, 0-250 microns, 0-225 microns, 0-200 microns, 0-175 microns, 0-150 microns, 0-125 microns, 0-100 microns, 0-75 microns, 0-50 microns, 0-25 microns, or 0-10 microns of the eggshell type catalyst's exterior surface. In some embodiments, the palladium nanoparticles of the noble metal shell may be located or concentrated within about 300 microns, about 275 microns, about 250 microns, about 225 microns, about 200 microns, about 175 microns, about 150 microns, about 125 microns, about 100 microns, about 75 microns, about 50 microns, about 25 microns, or about 10 microns of the eggshell type catalyst's exterior surface.

In many embodiments, about 90 percent of the catalytic palladium nanoparticles or nano-sized particles are located within about 300 microns of an exterior surface. In other embodiments, about 90 percent of the catalytic palladium nanoparticles or nano-sized particles are located within about 200 microns of an exterior surface. In other embodiments, about 90 percent of the catalytic palladium nanoparticles or nano-sized particles are located within about 100 microns of an exterior surface.

In some embodiments, the reducing agent comprises about 10% hydrogen at about 20 SCCM in helium at about 180 SCCM to produce nano-sized particles of the zero-valent noble metal having a particle size of less than about 2 nm. The term, "SCCM", as used herein, stands for standard cubic centimeters per minutes and represents a given flow rate for a gas or a gas mixture. In other embodiments, the reducing agent comprises hydrogen. Examples of other gases that may be added in addition to the hydrogen include, but are not limited to, helium, nitrogen, argon, xenon, and combinations thereof. The SCCM units, as used herein, are given relative to using 5 g of catalyst. A person skilled in the art could modify the gas flow rate depending on the amount of catalyst and reactor dimensions being used.

In other embodiments, the reducing agent comprises about 50% v/v alcohol and about 50% v/v water to produce nano-sized particles of the zero-valent palladium having a particle size of less than about 5 nm. In some examples, the reducing agent comprises about 50% v/v methanol and about 50% v/v water to produce nano-sized particles of the zero-valent noble metal having a particle size of about less than 5 nm. The term, "v/v", as used herein, means volume/volume and is used when two liquids are mixed together. For example, an about 50% v/v alcohol and about 50% v/v water mixture would contain equal volumes of alcohol and water. Examples of alcohols that can be used as the reducing agent include, but are not limited to, methyl alcohol, methanol, ethyl alcohol, ethanol, isopropanol, propyl alcohol, propanol, isobutanol, tert-butanol, n-butanol, pentanol, hexanol, heptanol, octanol, decanol, or mixtures thereof. The percentage v/v of alcohol or multiple alcohols mixed with water can vary and can be about 5% v/v, about 10% v/v, about 15% v/v, about 20% v/v, about 25% v/v, about 30% v/v, about 35% v/v, about 40% v/v, about 45% v/v, about 50% v/v, about 55% v/v, about 60% v/v, about 65% v/v, about 70% v/v, about 75% v/v, about 80% v/v, about 85% v/v, about 90% v/v, about 95% v/v, and about 100% v/v. In other embodiments, the alcohol may be mixed with a miscible organic solvent or the alcohol may be mixed with both water and a miscible organic solvent.

In other embodiments, the reducing agent comprises about 67% v/v hydrazine and about 33% v/v acetone to produce nano-sized particles of the zero-valent palladium having a particle size of less than about 7 nm. The percentage v/v of hydrazine mixed with acetone or any other solvent or mixture of solvents can be about 5% v/v, about 10% v/v, about 15% v/v, about 20% v/v, about 25% v/v, about 30% v/v, about 35% v/v, about 40% v/v, about 45% v/v, about 50% v/v, about 55% v/v, about 60% v/v, about 65% v/v, about 70% v/v, about 75% v/v, about 80% v/v, about 85% v/v, about 90% v/v, about 95% v/v, and about 100% v/v hydrazine. In yet other embodiments, the hydrazine may be mixed with other organic solvents.

Various types of chemical reducing agents may be used to control the nanoparticle size. Examples of some reductants include, but are not limited to, alcohol dehydrogenase (ADH), boranes, borane-tetrahydrofuran, catecholborane, copper hydride, low valent copper, low valent chromium, diisobutylaluminium hydride (DIBAL-H), diethyl 1,4-dihydro-2,6-dimethyl-3,5-pyridinedicarboxylate (Hantzsch ester), diisobutylaluminum hydride, diisopropylaminoborane, 1,3-dimethylimidazol-2-ylidene borane, dimethylsulfide borane (DMSB), formaldehyde, formic acid, hydrazine, hydrogen, low valent indium, iron, isopropanol, lithium, lithium aluminum hydride (LAH), lithium tetrahydridoaluminate, lithium triethylborohydride (LiTEBH or superhydride), magnesium, manganese, 3-mercaptopropionic acid (3-MPA), low valent neodymium, nickel, nickel borohydride, low valent niobium, 2-nitrobenzenesulfonylhydrazide (NBSH), phenylsilane, pinacolborane, polymethylhydrosiloxane (PMHS), potassium, potassium borohydride, potassium iodide, potassium tetrahydroborate, 2-propanol, low valent samarium, silanes, sodium, sodium borohydride, sodium cyanoborohydride, sodium dithionite, sodium hydrosulfite, sodium tetrahydroborate, sodium triacetoxyborohydride, strontium, tetramethyldisiloxane (TMDSO or TMDS), tin hydrides, low valent titanium, tributylstannane, tributyltin hydride, tricholorosilane, triethylphosphine, triphenylphosphine, triphenylphosphite, triethylsilane, tris(trimethylsilyl)silane (TTMSS), zinc, and combinations or mixtures thereof.

The catalyst loading describes the weight % of palladium or noble metals added to the solid support. As the catalyst loading is increased, the layer of palladium or noble metal nanoparticles thickens while the nanoparticle size remains limited to the type of reducing agent used to reduce the palladium or noble metal to its zero-valent state. In some embodiments, the catalyst loading can range from 0.1 weight % to 10 weight %. In other embodiments, the catalyst loading can range from 0.1 weight % to 0.5 weight %. In other embodiments, the catalyst loading can be about 0.5 weight % or about 1 weight %. In other embodiments, the catalyst loadings can be about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, about 1.0 weight %, about 2.0 weight %, about 3.0 weight %, about 4.0 weight %, and about 5.0 weight %.

Metallic nanoparticles can be used to limit dispersion effects and maximize the catalytic surface area of the active metal. A nanoparticle is a particle less than 100 nanometers (nm) in size. Most catalysts have a metallic particle size ranging between 1 and 10 nm with the smallest metal particle size being 2 nm or greater. Typically, a size of 2 nm is considered desirable in catalyst compositions, although a 5 nm or 7 nm particle can be utilized to tune reactivity or remove impurities present in a reaction. Palladium nanoparticles produced herein by the various reducing agents may have sizes greater than 0 and less than about 10 nanometers. Additional particles size ranges that may be produced with the disclosed reducing agents herein include, but are not limited to, about 0.1 to about 7 nm, about 0.1 to about 5 nm, about 0.1 to about 2.5 nm, about 0.1 to about 2 nm, about 0.1 to about 1.5 nm, about 0.1 to about 1 nm, about 0.1 to about 0.75 nm, about 0.1 to about 0.5 nm, about 1 to about 2 nm, about 1 to about 2.5 nm, about 0.5 to about 2 nm, about 0.5 to about 2.5 nm, about 2 to about 7 nm, about 3 to about 6 nm, about 4 to about 6 nm, about 5 to about 6 nm, about 2 to about 5 nm, about 3 to about 10 nm, about 3 to about 9 nm, about 5 to about 9 nm, about 5 to about 7 nm, about 7 to about 9 nm, about 6 to about 7 nm, about 6 to about 8 nm, or about 9 to about 10 nm.

In some embodiments, the size of the palladium nanoparticles in the noble metal shell may be less than about 2 nm, less than about 5 nm, less than about 7 nm, may be about 2 nm, may be about 5 nm, or may be about 7 nm. In other embodiments, the palladium nanoparticles in the noble metal shell may be less than about 2 nm, from about 1.5 nm to about 2 nm, or from about 1 nm to about 2 nm.

The present invention provides in a second embodiment a method for the single step synthesis of 2-ethylhexanal comprising: contacting n-butyraldehyde and a hydrogen gas with a palladium on titania eggshell type catalyst under vapor-phase condensation conditions to obtain a reaction product comprising 2-ethylhexanal; wherein the palladium eggshell catalyst comprises a palladium shell deposited on a titania support comprising nano-sized particles of palladium having a diameter less than about 10 nanometers; and wherein the palladium shell deposited on the titania support is concentrated within about 300 micrometers of the palladium eggshell type catalyst's exterior surface.

It is understood that the descriptions outlining and teaching the method for preparing an eggshell type catalyst previously discussed, which can be used in any combination, apply equally well to the second embodiment of the invention, where applicable, disclosing a method for the single step synthesis of 2-ethylhexanal.

The reaction or condensation of n-butyraldehyde with the palladium on titania eggshell type catalyst to form 2-ethylhexanal or a 2-ethylhexanal derivative is performed in a single step reaction under hydrogen. Unlike the synthetic methodologies disclosed in the art that synthesize 2-ethylhexanal in two separate steps, an aldol condensation followed by a hydrogenation reaction, or perform the synthesis in a one-pot reaction but with two different or separate catalysts sources, this inventive method uses a single catalyst to perform both the aldol condensation and the subsequent selective hydrogenation reaction in a one-pot single step reaction. The phrase, "one step reaction", as used herein, means that both the aldol condensation and the subsequent hydrogenation reaction occur in the same reaction environment without transferring additional materials to or from the reaction.

Vapor-phase condensation conditions are the temperature and pressure parameters that promote the chemical reaction of n-butyraldehyde with itself in the vapor phase to form a 2-ethylhexanal derivative together with the loss of a water molecule. The temperature used for the vapor-phase condensation is between about 200° C. and about 400° C., between about 220° C. and about 375° C., and between about 260° C. and about 320° C. In some embodiments, the temperature is about 250° C., about 290° C., or about 320° C. The reaction is normally run at atmospheric pressure or between about 0.1 and about 10.0 bars absolute (bara), between about 0.5 and about 5.0 bara, or between about 1.0 and 1.5 bara.

The n-butyraldehyde is contacted with the palladium on titania eggshell catalyst in the presence of a hydrogen gas. This hydrogen gas can be combined with an inert carrier gas such as nitrogen or helium. Gases recycled from the process can be used. The hydrogen gas component relative to the inert gas can be present at concentrations between 0.1 and 100 mole percent of the total gas feed, between about 2 and about 50 mole percent, and between about 5 and about 30 mole percent. Correspondingly, the inert gas component can be present at concentrations between 0 and about 99.9 mole percent of the total gas feed, between about 50 and about 98 mole percent, and between about 70 and about 95 mole percent. A higher partial pressure of hydrogen can have the deleterious effect of decarbonylation of the various 2-ethylhexanal species to undesirable heptenes. The use of lower hydrogen partial pressures can result in the formation of less 2-ethylhexanal relative to 2-ethylhexenal. Gases recycled from the process can be used as a portion of the hydrogen feed. In the event of inhibitory coke formation, the catalyst may be regenerated between reaction runs in air at 400° C. to 450° C.

In certain embodiments of the process of the invention, the liquid feed rate can range from 1.0 to 1000 mL/kg catalyst/minute or from 10 to 100 mL/kg catalyst/minute. In other embodiments, the liquid feed rate can range from 0.1 mL/kg catalyst/minute to 10.0 mL/kg catalyst/minute.

It is important that both a high conversion and selectivity is obtained for the palladium on titania eggshell type catalyst for the synthesis of 2-ethylhexanal. For example, the reaction of n-butyraldehyde with a palladium on titania eggshell type catalyst to make 2-ethylhexanal can have a n-butyraldehyde conversion of at least 70%, at least 80%, or at least 90%.

The reaction of n-butyraldehyde with a palladium on titania eggshell type catalyst to make 2-ethylhexanal can produce heptenes with a selectivity of less than 35%, less than 30%, less than 25%, less than 20%, less than 15%, or less than 10%. In some embodiments, the percent selectivity of heptenes in the 2-ethylhexanal reaction is about 45%, about 35%, about 30%, about 25%, or about 5%. The heptenes percent selectivity is defined as the amount of heptenes relative to the total amount of heptenes, n-butanol, 2-ethylhexenal, 2-ethylhexanal, and 2-ethylhexanol.

The reaction of n-butyraldehyde with a palladium on titania eggshell type catalyst to make 2-ethylhexanal can produce n-butanol with a selectivity of less than 20%, less than 15%, less than 10%, less than 5%, less than 3%, less than 2%, or less than 1%. In some embodiments, the percent selectivity of n-butanol in the 2-ethylhexanal reaction is about 20%, about 10%, about 5%, about 2%, or about 1%. The n-butanol percent selectivity is defined as the amount of n-butanol relative to the total amount of heptenes, n-butanol, 2-ethylhexenal, 2-ethylhexanal, and 2-ethylhexanol.

The reaction of n-butyraldehyde with a palladium on titania eggshell type catalyst to make 2-ethylhexanal can produce 2-ethylhexenal with a selectivity less than 90%, less than 80%, less than 70%, less than 60%, and less than 50%. In some embodiments, the percent selectivity of 2-ethylhexenal in the 2-ethylhexanal reaction is about 90%, about 60%, and about 1%. The 2-ethylhexenal percent selectivity is defined as the amount of 2-ethylhexenal relative to the total amount of heptenes, n-butanol, 2-ethylhexenal, 2-ethylhexanal, and 2-ethylhexanol.

The reaction of n-butyraldehyde with a palladium on titania eggshell type catalyst to make 2-ethylhexanal can produce 2-ethylhexanal with a selectivity greater than 20%, greater than 25%, greater than 30%, greater than 35%, greater than 40%, greater than 45%, greater than 50%, and greater than 60%. In some embodiments, the percent selectivity of 2-ethylhexanal in the 2-ethylhexanal reaction is about 50%, about 45%, about 40%, about 35%, about 30%, about 25%, and about 20%. The 2-ethylhexanal percent selectivity is defined as the amount of 2-ethylhexanal relative to the total amount of heptenes, n-butanol, 2-ethylhexenal, 2-ethylhexanal, and 2-ethylhexanol.

The reaction of n-butyraldehyde with a palladium on titania eggshell type catalyst to make 2-ethylhexanal can produce 2-ethylhexanol with a selectivity of less than 10%, less than 9%, less than 8%, less than 7%, less than 6%, less than 5%, less than 4%, less than 3%, less than 2%, or less than 1%. In some embodiments, the percent selectivity of 2-ethylhexanol in the 2-ethylhexanal reaction is about 10%, about 9%, about 8%, about 5%, and about 2%. The 2-ethylhexanol percent selectivity is defined as the amount of 2-ethylhexanol relative to the total amount of heptenes, n-butanol, 2-ethylhexenal, 2-ethylhexanal, and 2-ethylhexanol.

In some embodiments, the reaction of n-butyraldehyde with a palladium on titania eggshell type catalyst to make 2-ethylhexanal yields a 75% total n-butyraldehyde conversion with a 9% selectivity to heptenes, a 2% selectivity to n-butanol, a 58% selectivity to 2-ethylhexenal, a 30% selectivity to 2-ethylhexanal, and a 1% selectivity to 2-ethylhexanol.

Any combination of the conversion and selectivity values listed here is possible for the hydrogenation of an unsaturated compound with a palladium eggshell type catalyst with a particle size of about 2 nanometers, about 5 nanometers, or about 7 nanometers.

In some embodiments, the eggshell catalyst is tuned to have the desired catalytically active metal surface area (i.e. dispersion of metal) with a palladium metal shell. This palladium eggshell catalyst exhibits high turnovers while also being suitable for reactions that are heat and mass transfer limited. These disclosed palladium eggshell catalysts can have palladium shells comprising palladium nanoparticles having about 2 nm, about 5 nm, or about 7 nm sizes depending on the type and method of reducing agent used.

In some embodiments, examples of the palladium salt can include, but are not limited to, palladium acetate, palladium bromide, palladium chloride, palladium cyanide, palladium iodide, palladium nitrate, palladium sulfate, tetraaminepalladium bromine, tetraaminepalladium chloride, (ethylenediamine)palladium(II) chloride, or combinations thereof. In other embodiments, the palladium salt comprises palladium acetate, palladium bromide, palladium chloride, palladium cyanide, palladium iodide, palladium nitrate, palladium sulfate, or combinations thereof. In yet other embodiments, the palladium salt is palladium acetate.

Dissolving a palladium salt in a solvent to produce a palladium salt-containing solution can be performed at a variety of concentrations and conditions. For example, the palladium salt can be dissolved in the solvent to form an about 0.1% to about 20% by weight, an about 0.1% to about 10% by weight, or an about 0.2% to about 5% by weight of the palladium salt in a solvent to produce a palladium salt-containing solution. The salt-containing solution can be made at atmospheric pressure and at any temperature from 0° C. up to the boiling point of the solvent used. The phrase "dissolving", as used herein, means for the palladium salt to pass into solution and become part of the liquid phase; the palladium salt may completely dissolve or only partially dissolve into the solvent. In one embodiment, the palladium salt is completely dissolved into a solvent to produce a palladium salt-containing solution. In some embodiments, the palladium acetate salt is completely dissolved into a solvent to produce a palladium acetate-containing solution.

The wetness impregnation method comprises mixing the palladium salt-containing solution with a solid oxide support under atmospheric pressure for a limited amount of time at a given temperature. To effectively impregnate the solid oxide support, the palladium salt-containing solution and solid oxide support should be shaken or mixed together for about 5 seconds to about 30 minutes, about 5 seconds to about 15 minutes, about 5 seconds to about 10 minutes, about 5 seconds to about 5 minutes, about 5 seconds to about 1 minute, or for about 30 minutes, about 25 minutes, about 20 minutes, about 15 minutes, about 10 minutes, about 5 minutes, about 1 minute, about 45 seconds, about 30 seconds, or about 15 seconds. The temperature for the wetness impregnation method can be any temperature from about 0° C. up to the boiling point of the solvent used. In some embodiments, it can be useful to incorporate the palladium salt-containing solution with a solid oxide support that has a complimentary pore volume to produce a palladium salt-deposited support with varying thicknesses of the noble metal salt.

The solid oxide support comprises titanium dioxide, titanium (IV) oxide, titania, or $TiO_2$. Each of these titanium dioxide, titanium (IV) oxide, titania, and $TiO_2$ materials exist and can be used in the anatase, rutile, and brookite mineral forms. In some embodiments, the titanium dioxide, titanium (IV) oxide, titania, and $TiO_2$ materials are used in the anatase form. In some embodiments, the titanium dioxide, titanium (IV) oxide, titania, and $TiO_2$ materials are used in a mixture of the anatase and rutile forms. In some embodiments, the solid oxide support is titania in the anatase mineral form. The supports should be physically robust and pre-shaped. The term "pre-shaped" is used in this context to mean that the shape of the final catalyst is essentially the same as the starting support. The pre-shaped oxides typically can have average particle diameter sizes ranging from about 0.1 millimeter (mm) to about 20 mm. They can be in any common form such as extrudates, compressed pellets, or bulk solid that has been pulverized to the desired mesh size. They may also be in a variety of shapes such as rods, stars, cylinders, spheres, or broken chunks. Many of these oxide supports are available commercially, and their use simplifies the preparation of the catalyst composition of the invention, although this is not a requirement of the invention.

After the removal of the solvent from the palladium salt-containing solution and solid oxide support, a palladium salt-deposited oxide support remains. This palladium salt-deposited oxide support may comprise any combination of palladium salts listed herein coated on the surface of any of the titanium solid oxide supports listed herein. In some embodiments, the noble metal-salt-deposited oxide support comprises palladium acetate on a titania solid oxide support.

A majority of the palladium nanoparticles making up the palladium shells of these eggshell catalysts are located within about 300 micrometers ("microns") from the exterior surface of the catalyst composition to form an eggshell distribution. The term, "majority", as used herein, means that more particles are located within a given range than the amount of particles located outside of the range. For example, 50.01% or more of the palladium nanoparticles of the palladium shell may be located or concentrated within 0-300 microns, 0-275 microns, 0-250 microns, 0-225 microns, 0-200 microns, 0-175 microns, 0-150 microns, 0-125 microns, 0-100 microns, 0-75 microns, 0-50 microns, 0-25 microns, or 0-10 microns of the eggshell type catalyst's exterior surface. In one embodiment, the palladium nanoparticles of the palladium shell may be located or concentrated within about 300 microns, about 275 microns, about 250 microns, about 225 microns, about 200 microns, about 175 microns, about 150 microns, about 125 microns, about 100 microns, about 75 microns, about 50 microns, about 25 microns, or about 10 microns of the eggshell type catalyst's exterior surface In some embodiments, the reducing agent comprises about 10% hydrogen at about 20 SCCM in helium at about 180 SCCM to produce nano-sized particles of the zero-valent palladium having a particle size of less than about 2 nm. The term, "SCCM", as used herein, stands for standard cubic centimeters per minutes and represents a given flow rate for a gas or a gas mixture. In another embodiment, the reducing agent comprises hydrogen. Examples of other gases that may be added in addition to the hydrogen include, but are not limited to, helium, nitrogen, argon, xenon, and combinations thereof.

In other embodiments, the reducing agent comprises about 50% v/v alcohol and about 50% v/v water to produce nano-sized particles of the zero-valent palladium having a particle size of less than about 5 nm. In one example, the reducing agent comprises about 50% v/v methanol and about 50% v/v water to produce nano-sized particles of the zero-valent palladium having a particle size of about less than 5 nm. The term, "v/v", as used herein, means volume/volume and is used when two liquids are mixed together. For example, an about 50% v/v alcohol and about 50% v/v water mixture would contain equal volumes of alcohol and water. Examples of alcohols that can be used as the reducing agent include, but are not limited to, methyl alcohol, methanol, ethyl alcohol, ethanol, isopropanol, propyl alcohol, propanol, isobutanol, tert-butanol, n-butanol, pentanol, hexanol, heptanol, octanol, decanol, or mixtures thereof. The percentage v/v of alcohol or multiple alcohols mixed with water can vary and can be about 5% v/v, about 10% v/v, about 15% v/v, about 20% v/v, about 25% v/v, about 30% v/v, about 35% v/v, about 40% v/v, about 45% v/v, about 50% v/v, about 55% v/v, about 60% v/v, about 65% v/v, about 70% v/v, about 75% v/v, about 80% v/v, about 85% v/v, about 90% v/v, about 95% v/v, and about 100% v/v. In other embodiments, the alcohol may be mixed with a miscible organic solvent or the alcohol may be mixed with both water and a miscible organic solvent.

In other embodiments, the reducing agent comprises about 67% v/v hydrazine and about 33% v/v acetone to produce nano-sized particles of the zero-valent palladium having a particle size of less than about 7 nm. The percentage v/v of hydrazine mixed with acetone or any other solvent or mixture of solvents can be about 5% v/v, about 10% v/v, about 15% v/v, about 20% v/v, about 25% v/v, about 30% v/v, about 35% v/v, about 40% v/v, about 45% v/v, about 50% v/v, about 55% v/v, about 60% v/v, about 65% v/v, about 70% v/v, about 75% v/v, about 80% v/v, about 85% v/v, about 90% v/v, about 95% v/v, and about 100% v/v hydrazine. In other embodiments, the hydrazine may be mixed with other organic solvents.

The catalyst loading describes the weight % of palladium added to the solid support. As the catalyst loading is increased, the layer of palladium nanoparticles thickens while the nanoparticle size remains limited to the type of reducing agent used to reduce the palladium to its zero-valent state. In some embodiments, the catalyst loading can range from 0.1 weight % to 10 weight %. In other embodiments, the catalyst loading can range from 0.1 weight % to 0.5 weight %. In other embodiments, the catalyst loading can be about 0.5 weight % or about 1 weight %. In other embodiments, the catalyst loadings can be about 0.1 weight %, about 0.2 weight %, about 0.3 weight %, about 0.4 weight %, about 0.5 weight %, about 0.6 weight %, about 0.7 weight %, about 0.8 weight %, about 0.9 weight %, about 1.0 weight %, about 2.0 weight %, about 3.0 weight %, about 4.0 weight %, and about 5.0 weight %.

Palladium nanoparticle sizes produced herein by the various reducing agents may be greater than 0 and less than about 10 nanometers. Additional palladium particles size ranges that may be produced with the disclosed reducing agents include, but are not limited to, about 0.1 to about 7 nm, about 0.1 to about 5 nm, about 0.1 to about 2.5 nm, about 0.1 to about 2 nm, about 0.1 to about 1.5 nm, about 0.1 to about 1 nm, about 0.1 to about 0.75 nm, about 0.1 to about 0.5 nm, about 1 to about 2 nm, about 1 to about 2.5 nm, about 0.5 to about 2 nm, about 0.5 to about 2.5 nm, about 2 to about 7 nm, about 3 to about 6 nm, about 4 to about 6 nm, about 5 to about 6 nm, about 2 to about 5 nm, about 3 to about 10 nm, about 3 to about 9 nm, about 5 to about 9 nm, about 5 to about 7 nm, about 7 to about 9 nm, about 6 to about 7 nm, about 6 to about 8 nm, or about 9 to about 10 nm.

In some embodiments, the size of the palladium nanoparticles in the palladium shell may be less than about 2 nm, less than about 5 nm, less than about 7 nm, may be about 2 nm, may be about 5 nm, or may be about 7 nm. In another embodiment, the palladium nanoparticles in the palladium shell may be less than about 2 nm, from about 1.5 nm to about 2 nm, or from about 1 nm to about 2 nm.

One of the major applications for 2-ethylhexanal is its use as a raw material for perfumes. 2-Ethylhexanal can also be oxidized to 2-ethylhexanoic acid in a single step. The metallic salts of 2-ethylhexanoic acid are used as driers for odorless paints, inks, varnishes, and enamels.

The present invention provides in a third embodiment a method for the single step synthesis of 2-ethylhexanal comprising: contacting n-butyraldehyde and a hydrogen gas with a palladium on titania eggshell type catalyst under vapor-phase condensation conditions at about atmospheric pressure to obtain a reaction product comprising 2-ethylhexanal; wherein the palladium eggshell catalyst comprises about 0.1 weight % of a palladium metal shell deposited on a titania support comprising nano-sized particles of palladium having a diameter less than about 2 nanometers; and wherein the palladium shell deposited on the titania support is concentrated within about 300 micrometers of the palladium eggshell type catalyst's exterior surface.

It is understood that the descriptions outlining and teaching the method for preparing an eggshell type catalyst and the method for the single step synthesis of 2-ethylhexanal previously discussed, which can be used in any combination, apply equally well to the third embodiment of the invention, where applicable, further disclosing a method for the single step synthesis of 2-ethylhexanal.

The reaction or condensation of n-butyraldehyde with the palladium on titania eggshell type catalyst in a hydrogen gas to form 2-ethylhexanal or a 2-ethylhexanal derivative is performed in a single step reaction. This inventive method uses a single catalyst to perform both the aldol condensation and the subsequent selective hydrogenation reaction in a one-pot single step reaction.

Vapor-phase condensation conditions are the temperature and pressure parameters that promote the chemical reaction of n-butyraldehyde with itself in the vapor phase to form a 2-ethylhexanal derivative together with the loss of a water molecule. The temperature used for the vapor-phase condensation is between about 200° C. and about 400° C., between about 220° C. and about 375° C., and between about 260° C. and about 320° C. In some embodiments, the temperature is about 250° C., about 290° C., or about 320° C. The reaction is normally run at atmospheric pressure or between about 0.1 and about 10.0 bars absolute (bara), between about 0.5 and about 5.0 bara, or between about 1.0 and 1.5 bara.

The n-butyraldehyde is contacted with the palladium on titania eggshell catalyst in the presence of a hydrogen gas. This hydrogen gas can be combined with an inert carrier gas such as nitrogen or helium. Gases recycled from the process can be used. The hydrogenation gas component composition relative to the inert gas can be present at concentrations between 0.1 and 100 mole percent of the total gas feed, between about 2 and 50 mole percent, and between about 5 and 30 mole percent. Correspondingly, the inert gas component can be present at concentrations between 0 and 99.9 mole percent of the total gas feed, between about 50 and 98 mole percent, and between about 70 and 95 mole percent. A higher partial pressure of hydrogen can have the deleterious effect of decarbonylation of the various 2-ethylhexanal species to undesirable heptenes. The use of lower hydrogen partial pressures can result in the formation of less 2-ethylhexanal relative to 2-ethylhexenal. Gases recycled from the process can be used as a portion of the hydrogen feed. In the event of inhibitory coke formation, the catalyst may be regenerated between reaction runs in air at 400° C. to 450° C.

In certain embodiments of the process of the invention, the liquid feed rate can range from 1.0 to 1000 mL/kg catalyst/minute or from 10 to 100 mL/kg catalyst/minute. In other embodiments, the liquid feed rate can range from 0.1 mL/kg catalyst/minute to 10.0 mL/kg catalyst/minute.

It is important that both a high conversion and selectivity is obtained for the palladium on titania eggshell type catalyst for the synthesis of 2-ethylhexanal. For example, the reaction of n-butyraldehyde with a palladium on titania eggshell type catalyst to make 2-ethylhexanal can have a n-butyraldehyde conversion of at least 70%, at least 80%, or at least 90%.

The reaction of n-butyraldehyde with a palladium on titania eggshell type catalyst to make 2-ethylhexanal can produce heptenes with a selectivity of less than 35%, less than 30%, less than 25%, less than 20%, less than 15%, or less than 10%. In some embodiments, the percent selectivity of heptenes in the 2-ethylhexanal reaction is about 45%, about 35%, about 30%, about 25%, or about 5%. The heptenes percent selectivity is defined as the amount of heptenes relative to the total amount of heptenes, n-butanol, 2-ethylhexenal, 2-ethylhexanal, and 2-ethylhexanol.

The reaction of n-butyraldehyde with a palladium on titania eggshell type catalyst to make 2-ethylhexanal can produce n-butanol with a selectivity of less than 20%, less than 15%, less than 10%, less than 5%, less than 3%, less than 2%, or less than 1%. In some embodiments, the percent selectivity of n-butanol in the 2-ethylhexanal reaction is about 20%, about 10%, about 5%, about 2%, or about 1%. The n-butanol percent selectivity is defined as the amount of n-butanol relative to the total amount of heptenes, n-butanol, 2-ethylhexenal, 2-ethylhexanal, and 2-ethylhexanol.

The reaction of n-butyraldehyde with a palladium on titania eggshell type catalyst to make 2-ethylhexanal can produce 2-ethylhexenal with a selectivity less than 90%, less than 80%, less than 70%, less than 60%, and less than 50%. In some embodiments, the percent selectivity of 2-ethylhexenal in the 2-ethylhexanal reaction is about 90%, about 60%, and about 1%. The 2-ethylhexenal percent selectivity is defined as the amount of 2-ethylhexenal relative to the total amount of heptenes, n-butanol, 2-ethylhexenal, 2-ethylhexanal, and 2-ethylhexanol.

The reaction of n-butyraldehyde with a palladium on titania eggshell type catalyst to make 2-ethylhexanal can produce 2-ethylhexanal with a selectivity greater than 20%, greater than 25%, greater than 30%, greater than 35%, greater than 40%, greater than 45%, greater than 50%, and greater than 60%. In some embodiments, the percent selectivity of 2-ethylhexanal in the 2-ethylhexanal reaction is about 50%, about 45%, about 40%, about 35%, about 30%, about 25%, and about 20%. The 2-ethylhexanal percent selectivity is defined as the amount of 2-ethylhexanal relative to the total amount of heptenes, n-butanol, 2-ethylhexenal, 2-ethylhexanal, and 2-ethylhexanol.

The reaction of n-butyraldehyde with a palladium on titania eggshell type catalyst to make 2-ethylhexanal can produce 2-ethylhexanol with a selectivity of less than 10%, less than 9%, less than 8%, less than 7%, less than 6%, less than 5%, less than 4%, less than 3%, less than 2%, or less than 1%. In some embodiments, the percent selectivity of 2-ethylhexanol in the 2-ethylhexanal reaction is about 10%, about 9%, about 8%, about 5%, and about 2%. The 2-ethylhexanol percent selectivity is defined as the amount of 2-ethylhexanol relative to the total amount of heptenes, n-butanol, 2-ethylhexenal, 2-ethylhexanal, and 2-ethylhexanol.

In some embodiments, the reaction of n-butyraldehyde with a palladium on titania eggshell type catalyst to make 2-ethylhexanal yields a 75% total n-butyraldehyde conversion with a 9% selectivity to heptenes, a 2% selectivity to n-butanol, a 58% selectivity to 2-ethylhexenal, a 30% selectivity to 2-ethylhexanal, and a 1% selectivity to 2-ethylhexanol.

Any combination of the conversion and selectivity values listed here is possible for the hydrogenation of an unsaturated compound with a palladium eggshell type catalyst with a particle size of about 2 nanometers, about 5 nanometers, or about 7 nanometers.

The catalyst loading describes the weight % of palladium added to the solid oxide support. As the catalyst loading is increased, the layer of palladium nanoparticles thickens but the size of the nanoparticles remains limited to the type of reducing agent used to reduce the palladium to its zero-valent state. In some embodiments, the catalyst loading can range from 0.1 weight % to 10 weight % palladium. In other embodiments, the catalyst loading can range from 0.1 weight % to 0.5 weight % palladium. In other embodiments, the catalyst loading can be about 0.5 weight % or about 1 weight % palladium.

In some embodiments, the reducing agent comprises about 10% hydrogen at about 20 SCCM in helium at about 180 SCCM to produce nano-sized particles of the zero-valent palladium having a particle size of less than about 2 nm. The term, "SCCM", as used herein, stands for standard cubic centimeters per minutes and represents a given flow rate for a gas or a gas mixture. In another embodiment, the reducing agent comprises hydrogen. Examples of other gases that may be added in addition to the hydrogen include, but are not limited to, helium, nitrogen, argon, xenon, and combinations thereof.

Palladium nanoparticle sizes produced herein by the various reducing agents may be greater than 0 and less than about 10 nanometers. Additional palladium particles size ranges that may be produced with the disclosed reducing agents include, but are not limited to, about 0.1 to about 7 nm, about 0.1 to about 5 nm, about 0.1 to about 2.5 nm, about 0.1 to about 2 nm, about 0.1 to about 1.5 nm, about 0.1 to about 1 nm, about 0.1 to about 0.75 nm, about 0.1 to about 0.5 nm, about 1 to about 2 nm, about 1 to about 2.5 nm, about 0.5 to about 2 nm, about 0.5 to about 2.5 nm, about 2 to about 7 nm, about 3 to about 6 nm, about 4 to about 6 nm, about 5 to about 6 nm, about 2 to about 5 nm, about 3 to about 10 nm, about 3 to about 9 nm, about 5 to about 9 nm, about 5 to about 7 nm, about 7 to about 9 nm, about 6 to about 7 nm, about 6 to about 8 nm, or about 9 to about 10 nm.

There are also many different variations on the composition elements, reductants, reaction conditions, and reactants used that could be employed and would be obvious to one skilled in the art.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "$C_1$ to $C_5$ hydrocarbons", is intended to specifically include and disclose $C_1$ and $C_5$ hydrocarbons as well as $C_2$, $C_3$, and $C_4$ hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

It is to be understood that the mention of one or more process steps does not preclude the presence of additional process steps before or after the combined recited steps or intervening process steps between those steps expressly identified. Moreover, the lettering of process steps or ingredients is a convenient means for identifying discrete activities or ingredients and the recited lettering can be arranged in any sequence, unless otherwise indicated.

As used herein the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination.

As used in the specification and claims, the singular forms "a," "an" and "the" include their plural referents unless the context clearly dictates otherwise. For example, a reference to "a catalyst" or "a reductant" is synonymous with "at least one" or "one or more" catalysts or reductants and is thus intended to refer to both a single or a plurality of catalysts or reductants. In addition, references to a composition containing or including "an" ingredient is intended to include other ingredients or elements in addition to the one named.

The terms "containing" or "including" are intended to be synonymous with the word "comprising," meaning that at least the named compound, element, particle, or method step, etc., is present in the composition or article or method, but does not exclude the presence of other compounds, catalysts, materials, particles, method steps, etc., even if such compounds, materials, particles, method steps, etc., have the same function as what is named, unless expressly excluded in the claim.

Listing of Non-Limiting Embodiments

Embodiment A is a method for the single step synthesis of 2-ethylhexanal comprising: contacting n-butyraldehyde and a hydrogen gas with a palladium on titania eggshell type catalyst under vapor-phase condensation conditions to obtain a reaction product comprising 2-ethylhexanal; wherein the palladium eggshell catalyst comprises a palladium shell deposited on a titania support comprising nano-sized particles of palladium having a diameter less than about 10 nanometers; and wherein the palladium shell deposited on the titania support is concentrated within about 300 micrometers of the palladium eggshell type catalyst's exterior surface.

The method of Embodiment A wherein the nano-sized particles of palladium have a diameter of less than about 2 nanometers.

The method of Embodiment A or Embodiment A with any of the intervening features wherein the n-butyraldehyde and the palladium eggshell type catalyst are contacted at about atmospheric pressure.

The method of Embodiment A or Embodiment A with any one of the intervening features wherein the n-butyraldehyde and the palladium eggshell type catalyst are contacted at a temperature of about 290° C.

The method of Embodiment A or Embodiment A with any one of the intervening features wherein the reaction product comprises at least 30 weight % 2-ethylhexanal.

The method of Embodiment A or Embodiment A with any one of the intervening features wherein the conversion of n-butyraldehyde is at least 70%.

The method of Embodiment A or Embodiment A with any one of the intervening features wherein the palladium eggshell catalyst has 0.1 weight % palladium nanoparticles on the titania.

The method of Embodiment A or Embodiment A with any one of the intervening features wherein the palladium eggshell catalyst can be regenerated in air at a temperature from about 400° C. to about 450° C.

Embodiment B is a method for the single step synthesis of 2-ethylhexanal comprising: contacting n-butyraldehyde and a hydrogen gas with a palladium on titania eggshell type catalyst under vapor-phase condensation conditions at about atmospheric pressure to obtain a reaction product comprising 2-ethylhexanal; wherein the palladium eggshell catalyst comprises about 0.1 weight % of a palladium metal shell deposited on a titania support comprising nano-sized particles of palladium having a diameter less than about 2 nanometers; and wherein the palladium shell deposited on the titania support is concentrated within about 200 micrometers of the palladium eggshell type catalyst's exterior surface.

The method of Embodiment B wherein the n-butyraldehyde and the palladium on titania eggshell type catalyst are contacted to obtain a reaction mixture comprising at least 80 weight % 2-ethylhexanal, 2-ethylhexenal, and 2-ethylhexanol.

The method of Embodiment B or Embodiment B with any one of the intervening features wherein less than 10 weight % of the reaction product are heptenes.

The method of Embodiment B or Embodiment B with any one of the intervening features wherein the n-butyraldehyde and the palladium eggshell type catalyst are contacted at a temperature of about 290° C.

The method of Embodiment B or Embodiment B with any one of the intervening features wherein the conversion of n-butyraldehyde is at least 70%.

Embodiment C is a method for preparing a palladium eggshell type catalyst comprising: dissolving a palladium salt in a solvent to produce a palladium salt-containing solution; mixing the palladium salt-containing solution with a titania support under atmospheric pressure; removing said solvent to produce a palladium salt-deposited support; and reducing said palladium salt-deposited support to form a palladium eggshell type catalyst using a reducing agent selected from the group consisting of: hydrogen gas, hydrogen gas mixtures, alcohol solutions, alcohol/water solutions, hydrazine solutions, and hydrazine/solvent solutions; wherein the palladium shell deposited on the titania support comprises nano-sized particles of palladium having a diameter less than about 10 nanometers; and wherein the palladium shell deposited on the titania support is concentrated within about 300 micrometers of the eggshell type catalyst's exterior surface.

The method of Embodiment C wherein the reducing agent is about 10% hydrogen at about 20 SCCM in helium at about 180 SCCM.

The method of Embodiment C or Embodiment C with any one of the intervening features wherein the reducing agent is about 50% v/v methanol and about 50% v/v water.

The method of Embodiment C or Embodiment C with any one of the intervening features wherein the reducing agent is about 60% hydrazine and about 30% acetone.

The method of Embodiment C or Embodiment C with any one of the intervening features wherein the noble metal shells have a particle size of less than about 2 nm.

The method of Embodiment C or Embodiment C with any one of the intervening features wherein the noble metal shells have a particle size of less than about 5 nm.

The method of Embodiment C or Embodiment C with any one of the intervening features wherein the noble metal shells have a particle size of less than about 7 nm.

EXAMPLES

Materials

The support used was an anatase $TiO_2$ catalyst, as 3.2 mm pellets, obtained from a commercial supplier having a surface area of 36.8 $m^2$ g as calculated by the Brunnauer, Emmett and Teller (BET) theory using nitrogen gas as the absorbent. Palladium acetate ($Pd(OCOCH_3)_2$) (99.98%) and palladium chloride ($PdCl_2$)(99.9%) were obtained from Sigma Aldrich and used as palladium precursors without further purification. Acetone (Fisher Scientific), hydrazine (Sigma Aldrich) and deionized water were used as solvents without further purification.

Gas Chromatography Measurements

The nBuOH/2-ethylhexanal GC method used an internal standard calibrated weight % technique to accurately and precisely determine weight concentrations of approximately 30 analytes. Samples were prepared by weighing 0.1000 g accurately into a GC vial using an analytical balance. 1 mL of an internal standard solution was then added and the sample vortexed to mix. The oven program for the method used an 8° C./min temperature ramp and a final temperature of 200° C. Acetonitrile was used as the solvent for the method and diethylene glycol dimethyl ether (diglyme) was used as the internal standard. To separate all components, each sample was injected on two columns running in parallel on one instrument, a Shimadzu 2010 gas chromatograph with an AOC-20 autosampler. The concentration of heptenes, n-butanol, 2-ethylhexenal, 2-ethylhexanal, 2-ethylhexanol, and other analytes were detected using this approach using the TCD and/or FID detectors.

Methods and Procedures

Static volumetric or pulsed carbon monoxide (CO) chemisorption method was utilized to understand the metal dispersion on the oxide support using a Micrometrics ASAP 2020 or 2920 Analyzer. Initially the sample was heated to 250° C. in hydrogen flow to reduce the palladium and then CO adsorption isotherms were conducted at 35° C. The dispersion values reported here were from the difference algorithm which negates the CO adsorbed due to physisorption. Typically, the higher the dispersion numbers, the smaller the palladium particle size. To confirm the palladium particle size, Transmission Electron Microscope (TEM) measurements were undertaken on a JEOF4700F in a bright field mode. The palladium metal depth profile scans were done to clarify the egg-shell structure of these catalysts using a Scanning Electron Microscope (SEM).

Multiple hydrogenation experiments were conducted to confirm the industrial applicability of these novel egg-shell catalysts. Reaction parameters like conversions and selectivities are presented here for comparison purposes.

Examples 1-8: Synthesis and Catalytic Application of 0.1% Pd/TiO$_2$

Synthesis of 0.1% Pd/TiO$_2$ Catalyst:

This catalyst synthesized because it was expected to perform the dual steps previously carried out individually by the upstream titania catalyst and the downstream palladium catalyst. Wetness impregnation method was used to prepare this Pd/TiO$_2$ catalyst. Palladium acetate (0.022 g) was dissolved in 6 g of acetone and stirred for 10 minutes to completely dissolve the salt. This solution was immediately added to commercial TiO$_2$ (10 g) 3.2 mm pellets in a single neck round bottom flask. For effective impregnation, the flask was shaken for 30 seconds. This salt deposited support was evaporated with a rotovap at 80° C. for 30 minutes to remove the solvent. Finally the Pd(2+) salt was reduced to the zero-valent Pd(0) metal by 10% hydrogen (20 SCCM) in helium (180 SCCM) at 300° C. for 2 hours at a ramp rate of 5° C./min. After the hydrogen reduction step, the color of extrudates changed from orange to black indicating a reduction of Pd(2+) to zero-valent Pd(0).

Reaction:

The vapor phase experiments of n-butyraldehyde were performed at temperatures ranging from 250° C. to 320° C., 0.2 to 0.3 mL liquid feed/minute for various times. The catalyst amount was maintained constant in each reaction disclosed herein, at approximately 5 g, for comparison purposes. The performance of this 0.1% Pd/TiO$_2$ catalyst is summarized in performance Table 1 below. The catalyst was reduced in hydrogen prior to each use.

The vapor phase condensation reaction of n-butyraldehyde was performed in a 25 mm outer diameter (21 mm inner diameter) quartz reactor tube with length=79 cm (31 inches). Heat to the reactor was provided by an Applied Test Systems series 3210 three element electric furnace having a heated zone 54 cm (21.25 inches) in length. Liquid products were collected in a three necked flask fitted with a glycol chilled (0° C.) jacket and an additional dry ice trap. The third neck of the flask was connected to a side arm which was connected to a dry ice trap. The base of the main receiver flask and dry ice trap were fitted with a stopcock to allow for draining of the liquid products.

The quartz reactor had indentations 16 cm (6.25 inches) up from the base of the tube. The region of the reactor with the indentations was situated near the base of the heated section of the furnace. The reactor was also fitted with a thermowell that extended from the top of the reactor to about an inch below the indentations. The reactor was first loaded with quartz chips to about 8 inches in height above the indentations to allow the catalyst to be positioned in the middle of the 3 element furnace. The reactor was then loaded with an approximately 5 g charge of catalyst (0.1 weight % Pd/TiO$_2$). The three point thermocouple in the thermowell was placed 1.5 inches up from the base of the catalyst bed. Sufficient quartz chips were added to the region above the catalyst charge to reach the top of the heated region of the 3 element furnace. Liquid samples were collected over a measured time period, weighed and analyzed by gas chromatography.

As a substantial exotherm was observed in the first 10 minutes of the reaction, the sample collected after the first hour of reaction was discarded. The reaction activities and yields presented in performance Table 1 were collected over a period of approximately 3 hours after the initial 1 hour temperature stabilization period. The catalyst amount was maintained constant in all cases at approximately 5 g for comparison purposes. The catalyst was regenerated at 450° C. in air overnight between runs.

Reaction Parameter Definitions

Moles of n-Butyraldehyde (n-HBU) Reacted:

Initial moles of n-HBU—Final moles of n-HBU

Conversion of n-HBU:

$$\frac{\text{Moles of } n\text{-}HBU \text{ reacted}}{\text{Initial moles of } n\text{-}HBU} \times 100\%$$

Relative Selectivity of 2-Ethylhexanal:

$$\frac{\text{Moles of 2-ethylhexanal}}{\left(\begin{array}{l}\text{Moles of 2-ethylhexanal} + \text{moles of heptenes} + \\ \text{moles of } n\text{-butanol} + \text{moles of 2-ethylhexanal}\end{array}\right)} \times 100\%$$

TABLE 1

Experimental conditions for 2-ethylhexanal synthesis from n-butyraldehyde with a 0.1% Pd/TiO$_2$ catalyst. Total gas flow rate was 320 SCCM (nitrogen + hydrogen) and the liquid (n-butyraldehyde) flowrate was 0.2 ml/min

| Example | Temp./° C. | % H$_2$ | Liquid Mass Balance | $T_{rcv}$/° C. |
|---|---|---|---|---|
| 1 | 290 | 100 | 80.0 | 296.1 |
| 2 | 320 | 100 | 78.5 | 326.2 |
| 3 | 260 | 100 | 72.6 | 267.8 |
| 4 | 290 | 5 | 95.3 | 294.1 |
| 5 | 290 | 10 | 95.7 | 295.3 |
| 6 | 290 | 20 | 82.3 | 295.3 |
| 7 | 290 | 100 | 80.4 | 295.8 |
| 8 | 290 | 0 | 96.5 | 293.1 |

TABLE 2

2-Ethylhexanal synthesis from n-butyraldehyde with a 0.1% Pd/TiO$_2$ catalyst

| | | Selectivity/% | | | | |
|---|---|---|---|---|---|---|
| Example | Conversion/% | Heptenes | n-Butanol | 2-Ethylhexenal | 2-Ethylhexanal | 2-Ethylhexanol |
| 1 | 88.7 | 29 | 36.1 | 0.5 | 25 | 9.4 |
| 2 | 91.3 | 44.5 | 19 | 0.5 | 31.1 | 4.8 |
| 3 | 90.6 | 25.2 | 63.8 | 0.3 | 5.5 | 5.2 |
| 4 | 72.6 | 2.5 | 1 | 90.8 | 5.7 | 0 |
| 5 | 74.3 | 8.8 | 2 | 58.4 | 30.3 | 0.5 |
| 6 | 81.2 | 30.4 | 9.5 | 13 | 45.3 | 1.8 |
| 7 | 86 | 34.7 | 36.7 | 0.2 | 20.2 | 8.2 |
| 8 | 53.8 | 1 | 0.4 | 98.6 | 0 | 0 |

As can be seen from Table 2, the 0.1% Pd/TiO$_2$ catalyst is active towards the production of 2-ethylhexanal from n-butyraldehyde in a single step. Comparing Examples 1, 2 and 3, it was observed that at 320° C. significant amounts of heptenes are produced whereas at 260° C., n-butyraldehyde is hydrogenated to butanol while 290° C. seems to be the optimum temperature. Heptenes are produced from unfortunate decarbonylation of either 2-ethylhexenal (to 3-heptene) or decarbonylation and dehydrogenation of 2-ethylhexanal (to 2- or 3-heptene). See the proposed reaction mechanism below.

Scheme 2: Synthesis of undesired heptenes from desirable 2-ethylhexanal products

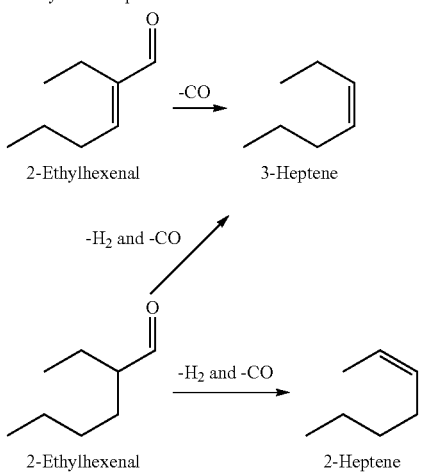

The optimum conditions found with these experiments was a temperature of 290° C., 320 SCCM of 10% hydrogen and 90% nitrogen flow and 0.2 ml/min n-butyraldehyde. At these conditions, a conversion of 74% was achieved at around 89% of useful selectivity with 30.3% selectivity to 2-ethylhexanal. Only 8.8% of heptenes were produced at these conditions. At lower hydrogen partial pressures (0% and 5%), little to no 2-ethylhexanal was produced. Higher hydrogen partial pressures (>10%) generated significant amounts of heptenes.

Comparing Examples 1 and 7 demonstrates that the catalyst activity is regenerable after an overnight regeneration step of calcination in air at 450° C. The average conversion of n-butyraldehyde and selectivity of 2-ethylhexanal are 87.4% (standard deviation of 1.9%) and 22.6% (standard deviation of 3.4%) respectively.

Example 8 is the control example which was conducted in the absence of hydrogen as a carrier gas (only 100% nitrogen) but the other conditions were similar to the successful Example 5. It can be seen that no 2-ethylhexanal could be generated in the absence of hydrogen as a carrier gas.

Examples 9-15: Synthesis and Catalytic Application of 0.5% Pd/TiO$_2$

Synthesis of 0.5% Pd/TiO$_2$ Catalyst:

The catalyst was prepared in the same way as Example 1 except that 0.11 g of palladium acetate was used instead of 0.02 g to give the desired palladium loading of 0.5% on titania.

Reaction:

The reactions were completed as described in Example 1 except that 5 g of the 0.5% Pd/TiO$_2$ was used as the catalyst. The catalyst was reduced in hydrogen prior to each use.

The results from these reactions carried out with the 0.5% Pd/TiO$_2$ are given in Tables 3 and 4.

TABLE 3

Experimental conditions for 2-ethylhexanal synthesis from n-butyraldehyde with a 0.5% Pd/TiO$_2$ catalyst. Variable gas flow rate of 100% hydrogen and variable liquid (n-butyraldehyde) flowrate

| | Conditions | | | | | |
|---|---|---|---|---|---|---|
| Example | Temp/ ° C. | Liquid Flow Rate/ ml · min$^{-1}$ | Gas Flow Rate/ SCCM | % H$_2$ | Liquid Mass Balance/% | T$_{rcr}$/ ° C. |
| 9 | 320 | 0.2 | 80 | 100 | 61.1 | 324.5 |
| 10 | 290 | 0.2 | 80 | 100 | 85.9 | 291.5 |
| 11 | 290 | 0.2 | 320 | 100 | 88.8 | 293.8 |
| 12 | 250 | 0.2 | 200 | 100 | 71.9 | 253.9 |
| 13 | 290 | 0.3 | 320 | 100 | 68.8 | 292.2 |
| 14 | 320 | 0.2 | 320 | 100 | 76.9 | 320.6 |
| 15 | 320 | 0.2 | 200 | 100 | 64.1 | 322.1 |

TABLE 4

2-Ethylhexanal synthesis from n-butyraldehyde with a 0.5% Pd/TiO₂ catalyst

| | | Selectivity/% | | | | |
|---|---|---|---|---|---|---|
| Example | Conversion/% | Heptenes | n-Butanol | 2-Ethylhexenal | 2-Ethylhexanal | 2-Ethylhexanol |
| 9 | 88.6 | 93.2 | 0.3 | 1 | 4.9 | 0.5 |
| 10 | 82.5 | 77.5 | 9.6 | 2.3 | 10.1 | 0.5 |
| 11 | 81.4 | 36.6 | 21.1 | 3.9 | 31.1 | 7.3 |
| 12 | 87.5 | 47 | 42.8 | 1 | 6.9 | 2.4 |
| 13 | 78.2 | 63.7 | 28.2 | 2 | 5.3 | 0.8 |
| 14 | 82.7 | 61.4 | 15.7 | 3.8 | 17.3 | 1.7 |
| 15 | 89.5 | 75.9 | 14.5 | 1.4 | 7.5 | 0.7 |

These examples were conducted with a higher loading of palladium on titania catalyst. Instead of 0.1% Pd loading, 0.5% Pd was utilized. This increased loading of Pd combined with the presence of 100% hydrogen, resulted in significant amounts of heptenes that were produced due to decarbonylation and dehydrogenation of 2-ethylhexanal derivatives. For example, in Example 9, 93% of the selectivity was lost to heptenes.

Comparative Examples 1-3: Synthesis and Catalytic Application of 4% Na, 0.1% Pd/SiO₂

Synthesis of 0.1% Pd/TiO₂ Catalyst:
The catalyst used in these examples using a similar procedure disclosed was prepared as shown in Kelly et al. Green Chemistry, 2002, 4, 392. Appropriate amounts of sodium and palladium nitrates were dissolved in water and the catalyst was synthesized using wetness impregnation of the salt solution on a silica support. The silica used as the support was obtained from Sigma-Aldrich and had a surface area of 5 m²/g. The catalyst was left overnight at room temperature and then dried at 90° C. Finally, the catalyst was calcined at 450° C. for 3 hours to burn the nitrates off the surface. This catalyst was then pressed into 8-by-14 mesh sized particles to be used in the reactor.

Reaction:
The reactions were completed as described in Example 1 except that 5 g of the 4% Na, 0.1% Pd/SiO₂ was used as the catalyst. The catalyst was reduced in hydrogen prior to each use.

Tables 5 and 6 present the results of feeding n-butyraldehyde with the 4% Na, 0.1% PdSiO₂ catalyst.

TABLE 5

Experimental conditions for 2-ethylhexanal synthesis from n-butyraldehyde with a 4% Na, 0.1% Pd/SiO₂ catalyst. Total gas flow rate was 320 SCCM (nitrogen + hydrogen) and the liquid (n-butyraldehyde) flowrate was 0.2 mL/min

| Comp. Example | Temp/° C. | % H₂ | Liquid Mass Balance/% | $T_{rctr}$/° C. |
|---|---|---|---|---|
| 1 | 290 | 0 | 97 | 291.5 |
| 2 | 290 | 10 | 90.1 | 291.4 |
| 3 | 290 | 100 | 96.5 | 291.2 |

TABLE 6

2-Ethylhexanal synthesis from n-butyraldehyde with a 4% Na, 0.1% Pd/SiO₂ catalyst

| | | Selectivity/% | | | | |
|---|---|---|---|---|---|---|
| Comp. Example | Conversion/% | Heptenes | n-Butanol | 2-Ethylhexenal | 2-Ethylhexanal | 2-Ethylhexanol |
| 1 | 5.1 | 0 | 0 | 100 | 0 | 0 |
| 2 | 10.8 | 0 | 0 | 100 | 0 | 0 |
| 3 | 0 | — | — | — | — | — |

Comparative Examples 4-5: Synthesis and Catalytic Application of Plain TiO₂

As an additional comparative catalyst, plain commercial TiO₂ (5 g) as 3.2 mm pellets was utilized. The crystal structure of the titania as detected using X-ray diffraction was noted to be the pure anatase polymorph of TiO₂. The surface area of this anatase titania catalyst was 36.8 m²/g as calculated by the Brunnauer, Emmett and Teller (BET) theory using nitrogen gas as the adsorbent. The pore volume and pore diameter from N₂ physisorption measurements was found to be 0.14 cm³/g and 150 Å respectively. This same titanium dioxide was used as the support for palladium in the earlier examples. No formation of 2-ethylhexanal was observed over just titania.

Reaction:
The reactions were completed as described in Example 1 except that 5 g of the plain commercial anatase titania was used as the catalyst. The catalyst was reduced in hydrogen prior to each use.

The results obtained from using the commercial TiO$_2$ catalyst on the n-butyraldehyde feed is given in Tables 7 and 8.

TABLE 7

Experimental conditions for 2-ethylhexanal synthesis from n-butyraldehyde with an anatase-TiO$_2$ catalyst. Total gas flow rate was 320 SCCM (nitrogen + hydrogen) and the liquid (n-butyraldehyde) flowrate was 0.2 mL/min

| Comp. Example | Temp/° C. | % H$_2$ | Liquid Mass Balance/% | T$_{rctr}$/° C. |
|---|---|---|---|---|
| 4 | 290 | 100 | 101.9 | 292.7 |
| 5 | 290 | 0 | 99.3 | 293.8 |

TABLE 8

2-Ethylhexanal synthesis from n-butyraldehyde with an anatase-TiO$_2$ catalyst

| | | Selectivity/% | | | | |
|---|---|---|---|---|---|---|
| Comp. Example | Conversion/% | Heptenes | n-Butanol | 2-Ethylhexenal | 2-Ethylhexanal | 2-Ethylhexanol |
| 4 | 65.7 | 0 | 0.8 | 98.7 | 0 | 0.5 |
| 5 | 58.6 | 0 | 0.4 | 99.6 | 0 | 0 |

Examples 16-17: Synthesis and Catalytic Application of 0.1% Pd/TiO$_2$ for the Synthesis of n-Butyraldehyde Synthesis of 0.1% Pd/TiO$_2$ Catalyst: The catalyst was prepared in the same way as Example 1 using 0.022 g of palladium acetate to give the desired palladium loading of 0.1% on titania.

Reaction:

The reactions were completed as described in Example 1 except that paraldehyde was used as a feed instead of n-butyraldehyde. The catalyst was reduced in hydrogen prior to each use. These examples were conducted to determine the scope of the tandem Aldol condensation and hydrogenation as demonstrated as described in the one step synthesis of 2-ethyl hexenal.

The results obtained from using the 0.1 Pd/TiO$_2$ catalyst with paraldehyde are presented in Tables 9 and 10.

Scheme 3: Synthesis of n-butyraldhyde from paraldehyde

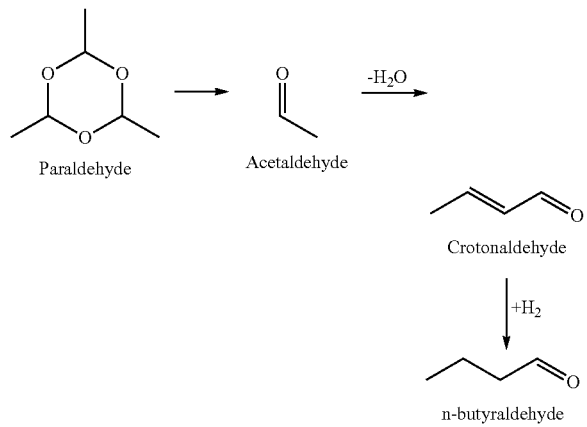

TABLE 9

Experimental conditions for n-butyraldehyde synthesis from paraldehyde with a 0.1% Pd/TiO$_2$ catalyst. Total gas flow rate was 320 SCCM (nitrogen + hydrogen) and the liquid (paraldehyde) flowrate was 0.2 mL/min

| Example | Temp/° C. | % H$_2$ | Liquid Mass Balance/% | T$_{rctr}$/° C. |
|---|---|---|---|---|
| 16 | 290 | 10 | 94 | 286.6 |
| 17 | 290 | 20 | 96 | 286.2 |

TABLE 10 n-Butyraldehyde synthesis from paraldehyde with a 0.1% Pd/TiO$_2$ catalyst

| | Product Composition/weight % | | | |
|---|---|---|---|---|
| Example | Acetaldehyde | Water | n-HBU | Crotonaldehyde |
| 16 | 64.01 | 6.05 | 2.35 | 9.14 |
| 17 | 59.69 | 7.52 | 4.80 | 7.49 |

Comparative Examples 6-7: Synthesis and Catalytic Application of Plain TiO$_2$

As a comparative catalyst for the synthesis of n-butyraldehyde from paraldehyde, a plain commercial TiO$_2$ (5 g) was utilized. The catalyst was used as obtained from the commercial source and described in Comparative Examples 4-5. No formation of n-butyraldehyde was observed using just the titania.

Reaction:

The reactions were completed as described in Example 16 except that 5 g of the plain commercial anatase titania was used as the catalyst instead of the palladium modified catalyst. The catalyst was reduced in hydrogen prior to each use The results obtained from Comparative Examples 6-7 using exclusively the commercial TiO$_2$ are given in Tables 11 and 12.

TABLE 11

Experimental conditions for attempted n-butyraldehyde synthesis from paraldehyde with an anatase $TiO_2$ catalyst. Total gas flow rate was 320 SCCM (nitrogen + hydrogen) and the liquid (paraldehyde) flowrate was 0.2 mL/min

| Comp. Example | Temp/ °C. | % $H_2$ | Liquid Mass Balance/% | $T_{rctr}$/° C. |
|---|---|---|---|---|
| 6 | 290 | 10 | 95 | 287.2 |
| 7 | 290 | 20 | 90 | 286.3 |

TABLE 12

Attempted n-butyraldehyde synthesis from paraldehyde with an anatase $TiO_2$ catalyst

| Comp. Example | Product Composition/weight % | | | |
|---|---|---|---|---|
| | Acetaldehyde | Water | n-HBU | Crotonaldehyde |
| 6 | 59.22 | 4.63 | 0.25 | 10.44 |
| 7 | 59.16 | 2.03 | 0.31 | 13.51 |

It is not intended that the scope of the invention is to be limited by the Examples described and illustrated above, but instead it is intended the scope of the invention will be determined by the appended claims and their equivalents.

What is claimed is:

1. A method for a single step synthesis of 2-ethylhexanal comprising: contacting n-butyraldehyde and a hydrogen gas with a palladium on titania eggshell type catalyst under vapor-phase condensation conditions to obtain a reaction product comprising 2-ethylhexanal;
    wherein the palladium eggshell catalyst comprises a palladium shell deposited on a titania support comprising nano-sized particles of palladium having a diameter less than about 10 nanometers; and
    wherein the palladium shell deposited on the titania support is concentrated within about 300 micrometers of the palladium eggshell type catalyst's exterior surface.

2. The method according to claim 1, wherein the nano-sized particles of palladium have a diameter of less than about 2 nanometers.

3. The method according to claim 1, wherein the n-butyraldehyde and the palladium eggshell type catalyst are contacted at about atmospheric pressure.

4. The method according to claim 1, wherein the n-butyraldehyde and the palladium eggshell type catalyst are contacted at a temperature of about 290° C.

5. The method according to claim 1, wherein the reaction product comprises at least 30 weight % 2-ethylhexanal.

6. The method according to claim 1, wherein the conversion of n-butyraldehyde is at least 70%.

7. The method according to claim 1, wherein the palladium eggshell catalyst has 0.1 weight % palladium nanoparticles on the titania.

8. The method according to claim 1, wherein the palladium eggshell catalyst can be regenerated in air at a temperature from about 400° C. to about 450° C.

9. A method for a single step synthesis of 2-ethylhexanal comprising: contacting n-butyraldehyde and a hydrogen gas with a palladium on titania eggshell type catalyst under vapor-phase condensation conditions at about atmospheric pressure to obtain a reaction product comprising 2-ethylhexanal;
    wherein the palladium eggshell catalyst comprises about 0.1 weight % of a palladium metal shell deposited on a titania support comprising nano-sized particles of palladium having a diameter less than about 2 nanometers; and
    wherein the palladium shell deposited on the titania support is concentrated within about 300 micrometers of the palladium eggshell type catalyst's exterior surface.

10. The method according to claim 9, wherein the n-butyraldehyde and the palladium on titania eggshell type catalyst are contacted to obtain a reaction mixture comprising at least 80 weight % 2-ethylhexanal, 2-ethylhexenal, and 2-ethylhexanol.

11. The method according to claim 9, wherein less than 10 weight % of the reaction product are heptenes.

12. The method according to claim 9, wherein the n-butyraldehyde and the palladium eggshell type catalyst are contacted at a temperature of about 290° C.

13. The method according to claim 9, wherein the conversion of n-butyraldehyde is at least 70%.

* * * * *